United States Patent [19]
Ishibashi et al.

[11] Patent Number: 6,080,405
[45] Date of Patent: Jun. 27, 2000

[54] FOAM PROTEINS AND USE THEREOF

[75] Inventors: Yoshihiko Ishibashi; Tatsufumi Kakui, both of Osaka; Kazuo Nakatani, Kyoto; Yoshitake Terano, Osaka, all of Japan

[73] Assignee: Suntory Limited, Osaka, Japan

[21] Appl. No.: 09/035,749

[22] Filed: Mar. 6, 1998

[30] Foreign Application Priority Data

Mar. 7, 1997 [JP] Japan ..................... 9-053249
Dec. 4, 1997 [JP] Japan ..................... 9-334229

[51] Int. Cl.$^7$ ............... A61K 39/395; G01N 33/53; C12P 21/04; C07K 16/00; A23B 4/12
[52] U.S. Cl. .............. 424/141.1; 99/278; 426/7; 435/7.1; 435/70.1; 435/70.2; 435/70.21; 436/547; 436/548; 530/388; 530/391.1
[58] Field of Search ............ 99/278; 424/141.1; 426/7; 435/7.1, 70.1, 70.2, 70.21; 436/547, 548; 530/388.1, 391.1

[56] References Cited

U.S. PATENT DOCUMENTS

| | | | |
|---|---|---|---|
| 3,911,089 | 10/1975 | Shiraishi et al. | 423/376 |
| 4,457,905 | 7/1984 | Ebner | 423/376 |
| 4,461,752 | 7/1984 | Sasaki et al. | 423/376 |
| 4,511,548 | 4/1985 | Attig et al. | 423/376 |
| 4,946,819 | 8/1990 | Sasaki et al. | 502/214 |
| 4,981,830 | 1/1991 | Sasaki et al. | 502/214 |
| 5,094,990 | 3/1992 | Sasaki et al. | 502/214 |
| 5,158,787 | 10/1992 | Sasaki et al. | 423/376 |

OTHER PUBLICATIONS

Asano, et al., "Isolation and Characterization of Foaming Proteins of Beer", Res. Lab. Kirin Brewery Co., Ltd., No. 23, 1980, pp. 1–13.

*Primary Examiner*—Rodney P. Swartz
*Attorney, Agent, or Firm*—Pillsbury Madison & Sutro

[57] ABSTRACT

Novel foam proteins, monoclonal antibodies specifically recognizing said proteins, a method for determining foam protein contents in beer samples by an immunoassay using said monoclonal antibodies, a method for determining head retention and head retention stability of beer, as well as a method for evaluating raw materials of beer and stabilizers for beer are disclosed. The novel foam proteins crucial for head retention of beer have molecular weights of about 40000 to about 48000 as determined by Western blot analysis.

3 Claims, 2 Drawing Sheets

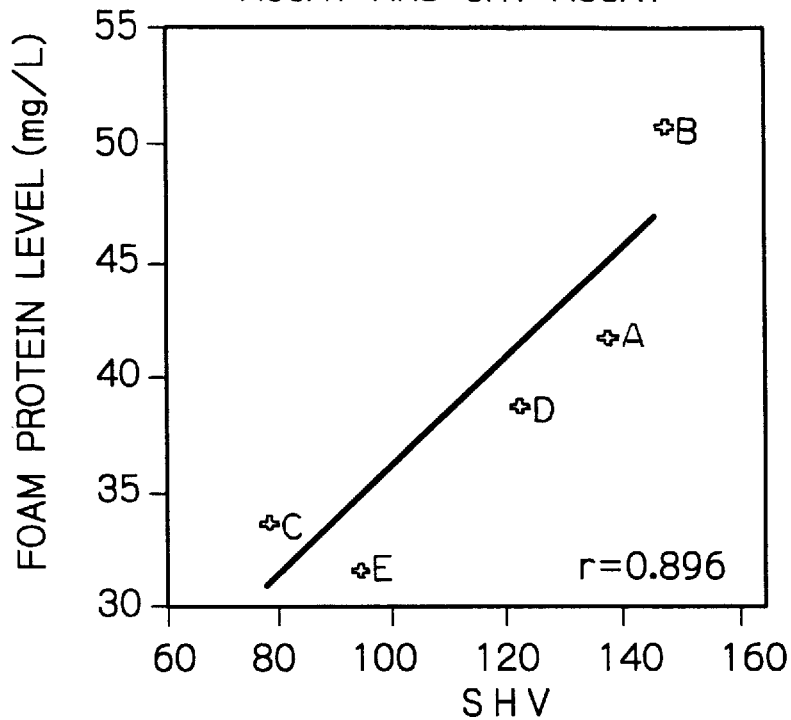
Fig. 1(A) CORRELATION BETWEEN PRIOR ASSAY AND SHV ASSAY
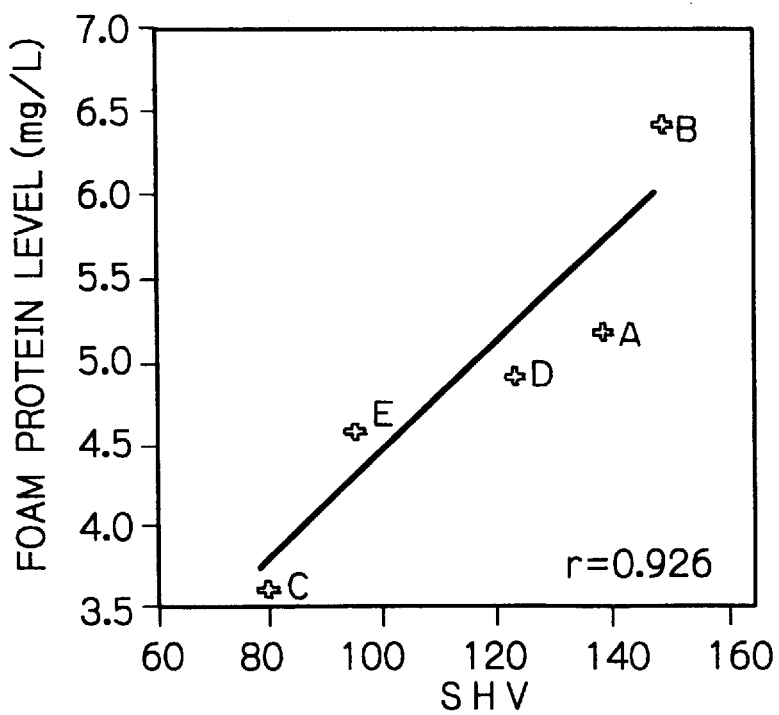
Fig. 1(B) CORRELATION BETWEEN SANDWICH ASSAY AND SHV ASSAY

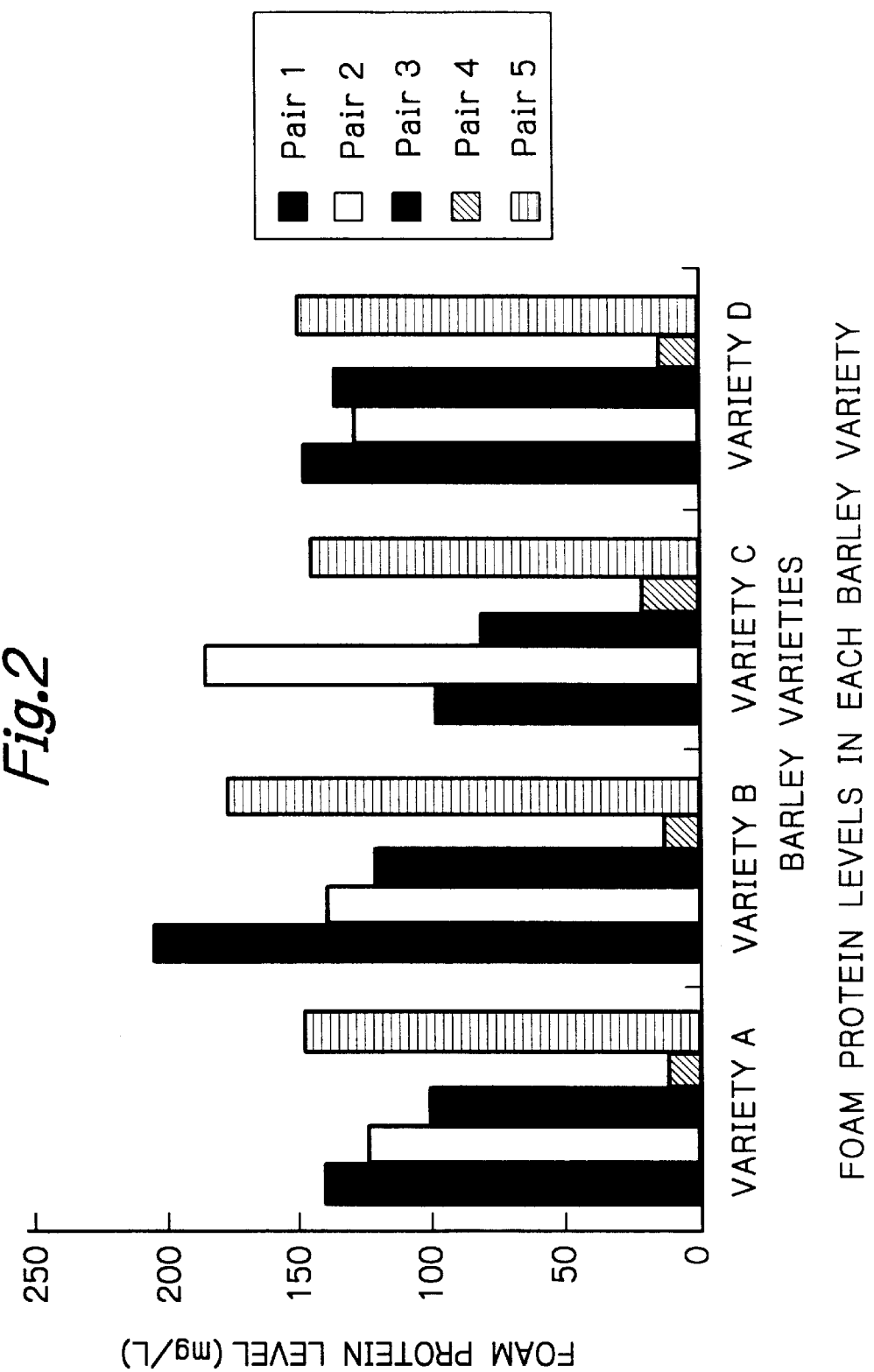

SEQUENCE LISTING

```
(1) GENERAL INFORMATION:

(iii) NUMBER OF SEQUENCES:  6

(2) INFORMATION FOR SEQ ID NO: 1:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO: 1:

Ala Val Glu Asn Ala Asn Arg Val Asn Lys Phe Leu Phe Leu Ile
                 5                  10                  15

Arg Glu Ala Ile (2) INFORMATION FOR SEQ ID NO: 2:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 2:

Phe Asn Pro Gly Gln Val Asp Gly Lys Met Leu Pro Tyr Leu Thr
                 5                  10                  15

(2) INFORMATION FOR SEQ ID NO: 3:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 3:

Val Tyr Pro Val Gln Tyr Ala Gly Gln Gly Leu Pro Leu Asn Gly
                 5                  10                  15

(2) INFORMATION FOR SEQ ID NO: 4:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 4:

Phe Asn Pro Val Gln Val Asp Ala Lys Met Pro Pro Leu Phe Leu
                 5                  10                  15

(2) INFORMATION FOR SEQ ID NO: 5:

(i) SEQUENCE CHARACTERISTICS:
        (A) LENGTH: 15 amino acids
        (B) TYPE: amino acid
        (D) TOPOLOGY: linear (ii) MOLECULE TYPE: peptide
```

-continued (xi) SEQUENCE DESCRIPTION: SEQ ID NO: 5:

Val Tyr Pro Pro Gln Tyr Pro Gly Met Gly Leu Ile Gln Asn Leu
              5                   10                  15

(2) INFORMATION FOR SEQ ID NO: 6:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (xi) SEQUENCE DESCRIPTION: SEQ ID NO: 6:

Asp Val Val Ala Asn Met Leu Pro Leu Phe Leu Ile
              5                   10

FOAM PROTEINS AND USE THEREOF

BACKGROUND OF THE INVENTION

The present invention relates to novel proteins as one of major ingredients crucial for head retention of beer, monoclonal antibodies against said proteins, and an assay for determining foam protein contents in final beer products or beer samples during the brewing process using said monoclonal antibodies. The present invention also relates to a method for determining head retention and head retention stability of beer as well as a method for evaluating raw materials of beer and stabilizers for beer, on the basis of said assay.

Beer is essentially made from malt by saccharifying it into wort, subjecting said wort to primary fermentation with yeast, then sending the resulting green beer to post-fermentation (conditioning) followed by filtration and packaging.

Among the most important qualities of appearance of beer brewed by this process is foam. This property is mainly defined by two aspects, i.e. foaming and head retention.

Head retention has been evaluated on the basis of physicochemical characteristics of foam such as disintegration speed of foam or adhesion to a glass surface. However, foam has complex properties so that sufficient reproducibility or accuracy is unable to be obtained on such a physicochemical basis. Moreover, raw materials of beer such as barley and malt or the stability of long-stored beer for head retention can be evaluated only after the beer has actually been brewed. Therefore, it has been desired to establish a reproducible and rapid evaluation method.

Thus, a method for determining head retention and head retention stability using polyclonal antibodies against raw foam proteins extracted from beer was developed (JPA No. 333223/95). However, this method involved comprehensively testing several foam proteins, and could not detect a minute amount of ingredient-specific foam proteins. Therefore, it has been desired to develop a better method with sufficient sensitivity to detect even a minute amount of ingredient-specific foam proteins.

SUMMARY OF THE INVENTION

The present invention was accomplished with the object of isolating and purifying a novel ingredient (foam protein) among major ingredients crucial for head retention of beer from raw foam proteins extracted from beer, preparing a monoclonal antibody directed to and specifically recognizing said novel foam protein, and providing an assay for rapidly and exactly determining foam protein contents by applying an immunoassay using said monoclonal antibody.

Another object of the present invention is to provide a method for determining head retention or head retention stability of beer using said assay.

Still another object of the present invention is to provide an evaluation method of raw materials of beer such as barley or malt and a selection method of stabilizers to be added so as to improve turbidity stability of beer using said assay.

BRIEF DESCRIPTION OF THE DRAWINGS

FIG. 1 shows a correlation between the foam protein level determined by the sandwich assay of the present invention or the prior assay and the SHV assay (A: correlation between the prior assay and the SHV assay; B: correlation between the sandwich assay of the present invention and the SHV assay).

FIG. 2 shows foam protein levels in barley malt varieties A, B, C, D as determined with monoclonal antibody pairs 1 to 5.

DETAILED DESCRIPTION OF THE INVENTION

In order to attain the above objects, six foam protein fractions were isolated from raw foam protein fractions and purified, with monoclonal antibodies then being prepared against the resulting foam proteins and said monoclonal antibodies being used to accomplish the present invention.

Isolation and purification of novel foam proteins of the present invention were performed by slightly modifying the procedure of Asano et al. (Rept. Res. Lab. Kirin Brewery Co., Ltd., No. 23, pp. 1–13 (1980)). Namely, a beer product immediately after brewing may be salted out with ethanol to give a precipitate, which is then subjected to various column chromatography steps (ion exchange and reverse phase chromatographies, gel filtration, etc.) to isolate and purify foam protein fractions. According to the present invention, six foam protein fractions were isolated and purified in this manner.

The resulting foam protein fractions were determined for their molecular weights by Western blot and their partial primary structures by an amino acid sequencer/mass spectrometer.

Foam protein 1 was further tested for its amino acid composition by acid hydrolysis with methanesulfonic acid.

Those foam proteins are characterized as follows:

(A) Foam protein 1
1) molecular weight of about 48000 as determined by Western blot analysis,
2) amino acid sequence shown in SEQ ID NO: 1,
3) amino acid composition shown in Table 1.

TABLE 1

|  | Ratio (%) |
| --- | --- |
| Thr/Gln | 5.8 |
| Ser/Asn | 10.0 |
| Glu | 13.3 |
| Pro | 3.2 |
| Gly | 9.4 |
| Ala | 11.5 |
| Cys | 0.6 |
| Val | 8.7 |
| Ile | 4.8 |
| Leu | 11.6 |
| Tyr | 0.8 |
| Phe | 5.9 |
| His | 4.1 |
| Lys | 5.9 |
| Trp | 1.4 |
| Arq | 2.8 |
| Total | 100.0 |

(B) Foam protein 2
1) molecular weight of about 48000 as determined by Western blot analysis;
2) amino acid sequence shown in SEQ ID NO: 2.

(C) Foam protein 3
1) molecular weight of about 40000 as determined by Western blot analysis;
2) amino acid sequence shown in SEQ ID NO: 3.

(D) Foam protein 4
1) molecular weight of about 40000 as determined by Western blot analysis;
2) amino acid sequence shown in SEQ ID NO: 4.

(E) Foam protein 5
1) molecular weight of about 40000 as determined by Western blot analysis;
2) amino acid sequence shown in SEQ ID NO: 5.
(F) Foam protein 6
1) molecular weight of about 47000 as determined by Western blot analysis;
2) amino acid sequence shown in SEQ ID NO: 6.

A search through the data bank "SWISS-PROT" proved that all these amino acid sequences are novel proteins.

Monoclonal antibodies which are specific for the foam proteins of the present invention can be prepared according to conventional procedures (see "Immunological Experiment Procedures II", pp. 945–957, Nankodo) by immunizing an animal with an antigen (each of the foam proteins above), recovering antibody-producing cells, fusing them to myelona cells, screening the fused cells and collecting hybridoma strains strongly reacting with the target antigen.

Thus obtained monoclonal antibodies can be used to determine foam protein contents in final beer products and beer samples during the brewing process by an immunoassay. The immunoassay includes radioimmunoassay, enzyme immunoassay, fluoroimmunoassay, luminescent immunoassay, turbidimetric immunoassay, etc., among which enzyme immunoassay, particularly ELISA (Enzyme-linked Immunosorbent Assay) is preferred because it provides highly sensitive detection of foam proteins and automatic determination of a number of samples.

According to ELISA, a monoclonal antibody of the present invention is first immobilized as a primary antibody on a support. The support is preferably a solid support, for example, in the form of a container such as an ELISA plate molded from a polymer such as styrene or polystyrene. Immobilization of the monoclonal antibody on a support can be accomplished by, for example, adsorbing the monoclonal antibody dissolved in a buffer such as carbonate or borate buffer to the support. A polyclonal antibody (such as the polyclonal antibodies described in JPA No. 333223/95) is used as a secondary antibody to perform sandwich ELISA. Alternatively, foam proteins can be detected more reliably and exactly by applying sandwich ELISA using one of the monoclonal antibodies of the present invention as a primary antibody and a different monoclonal antibody as a secondary antibody as described in Examples below.

An example of the assay for determining foam protein contents in beer according to the present invention is explained below.

At first, aliquots of a primary antibody are dispensed into microplates and incubated with an antibody-adsorbing buffer. After the supernatant is removed, the plates are washed with a washing solution. Similarly, a blocking solution, an intended antigen solution (beer solution), a secondary antibody and a labeling enzyme are successively dispensed, incubated and washed. Finally, a substrate solution is dispensed and incubated at room temperature or 37° C., then the absorbance at 405 nm is measured to calculate the concentration of the foam protein in the beer sample by using a calibration graph separately prepared from a standard dilution series of the foam protein.

The antibody-adsorbing buffer includes, for example, PBS(−) buffer, and the diluent includes, for example, PBS(−) buffer containing bovine serum albumin (BSA), gelatin or ovalbumin. The washing solution includes, for example, PBS(−) buffer containing $NaN_3$ and Tween 20, Tris-buffered physiological saline (TBS) containing NaCl and Tween 20, etc. The blocking solution includes, for example, PBS(−) buffer containing 1–3% BSA, PBS(−) buffer containing 1–5% skimmed milk, etc. The labeling enzyme includes, for example, peroxidase, acid phosphatase, alkaline phosphatase, β-galactosidase, etc. The substrate solution can be appropriately selected to suit the labeling enzyme, e.g. disodium p-nitrophenylphosphate salt (PNPP) for alkaline phosphatase or o-nitrophenyl β-D galactosidase for β-galactosidase.

Head retention and head retention stability of beer can be evaluated by determining foam protein contents in final beer products and beer samples during the beer brewing process as described above.

It is also important in beer brewing that various stabilizers such as silica gel or tannic acid added to improve turbidity stability or for other purposes should not adversely affect head retention. The assay of the present invention can also be applied to efficacy evaluation of such stabilizers. In an Example described below, for example, foam protein levels were determined by the ELISA assay of the present invention in the presence of various stabilizers added to a mash during the beer brewing process to reveal that the residual foam protein level varies with the type of stabilizer, thus proving that the assay of the present invention can be used to evaluate stabilizers.

Moreover, the assay of the present invention can be used to determine foam protein contents in raw materials of beer (barley and malted barley, etc.). Thus, the assay of the present invention allows the quality of raw materials of beer to be readily evaluated before brewing, though raw materials could previously be evaluated only after brewing.

The assay of the present invention uses one or two monoclonal antibodies for determination of foam proteins in beer samples to reduce variation among measurements and provides a sufficiently high sensitivity to detect even a minute amount of foam proteins. The assay of the present invention also shows a good correlation with the results of measurement by the prior head retention assay (SHV assay) as described in Comparative example 1 below, revealing that it can be effectively used to rapidly and exactly evaluate head retention and head retention stability of beer as an alternative to the prior assay.

The present invention also provides a kit for use in the methods of the present invention described above. The kit of the present invention comprises a monoclonal antibody specifically recognizing a foam protein of the present invention. The antibody may be diluted in said diluent or in a lyophilized form. In addition to said antibody, the kit of the present invention may further comprise a 96-well plate, a sample-adsorbing buffer, a washing solution, a blocking solution, a substrate solution, a dilution of a secondary antibody and a calibration graph, etc.

The present invention makes it possible to isolate and purify novel proteins which are crucial for head retention in beer. Moreover, the present invention made it possible to prepare monoclonal antibodies against said proteins and apply sandwich ELISA based on the antibodies for selecting the best malt or stabilizers for beer in terms of foam qualities or for evaluating optimal beer brewing conditions both exactly and rapidly.

The following examples illustrate the present invention in detail, but are not intended to limit the scope thereof. Various changes or modifications to the present invention with be apparent to those skilled in the art and included in the scope of the present invention.

EXAMPLES

Example 1

Preparation of foam proteins

Isolation and purification of foam protein 1

Raw foam protein fractions were ethanol precipitated from a final beer product (Suntory). After dialysis, these fractions were purified into active fractions by successively performing gel filtration (Toyopearl HW-55F) and ion exchange (Toyopearl G650M) chromatographies, and finally purified by repeating gel filtration HPLC (Toyopearl G2000SW) and reverse phase HPLC (Toyopearl C8). The purity of final fractions was ascertained by observing a single peak on HPLC chromatograms and a single band on SDS-PAGE. After column chromatography steps, the active fractions were evaluated by applying the procedure of Asano et al. (Rept. Res. Lab. Kirin Brewery Co., Ltd., No. 23, pp. 1–13, (1980)). Namely, a sample of 100–300 mg was dissolved in 1 L of a 3.6% aqueous ethanol solution (pH 4.2) and 20 ml of this solution was shaken in a graduated tube at 20° C. for 5 seconds (400 reciprocations/min). The volume of foam after shaking was measured and only high activity fractions were collected.

This foam protein had a molecular weight of about 48000 as measured by Western blot analysis.

The foam protein was determined by an amino acid sequencer to have a partial primary sequence of Ala-Val-Glu-Asn-Ala-Asn-Arg-Val-Asn-Lys-Phe-Leu-Phe-Leu-Ile-Arg-Glu-Ala-Ile (SEQ ID NO: 1). A search through the data bank "SWISS-PROT" revealed that this sequence is a novel protein.

The results of the amino acid composition analysis of this foam protein by acid hydrolysis with methansulfonic acid are as shown in Table 1 above.

Isolation and purification of foam proteins 2–6

Raw foam protein fractions were ethanol precipitated from a final beer product (Suntory). After dialysis, these fractions were concentrated and purified by ion exchange column (Toyopearl G650M) chromatography, gel filtration HPLC (Toyopearl G2000SW) and reverse phase HPLC (Toyopearl ODS) successively, to isolate several active fractions. The active fractions were purified by gel filtration and ion exchange chromatography successively. The purity of final fractions was evaluated by observing a single peak on SDS-PAGE. After column chromatography steps, the active fractions were evaluated in the same manner as described for foam protein 1 above.

The resulting five foam proteins (designated as foam protein 2, foam protein 3, foam protein 4, foam protein 5 and foam protein 6, respectively) had molecular weights of about 48000 (foam protein 2), about 40000 (foam protein 3), about 40000 (foam protein 4), about 40060 (foam protein 5) and about 47000 (foam protein 6), respectively as measured by Western blot analysis.

These foam proteins eluted after the following retention times during reverse phase HPLC under the following conditions.

Chromatography conditions

Column: TSK-Gel 80 Ts (6 mm I.D.×150 mm)
Elution conditions:
0–10 min. H$_2$O
10–40 min. H$_2$O→100% MeCN linear gradient
40–50 min. 100% MeCN.
Flow rate: 1.0 ml/min.
Detection condition: 280 nm (UV)

Retention time

Foam protein 2: 30–32 min.
Foam protein 3: 26–28 min.
Foam protein 4: 21–23 min.
Foam protein 5: 23–25 min.
Foam protein 6: 33–35 min.

The retention time of foam protein 1 chromatographed under the same conditions was 22–24 minutes.

Foam proteins 2 to 6 were determined by an amino acid sequencer to have partial primary structures of Phe-Asn-Pro-Gly-Gln-Val-Asp-Gly-Lys-Met-Leu-Pro-Tyr-Leu-Thr (foam protein 2, SEQ ID NO: 2), Val-Tyr-Pro-Val-Gln-Tyr-Ala-Gly-Gln-Gly-Leu-Pro-Leu-Asn-Gly (foam protein 3, SEQ ID NO: 3), Phe-Asn-Pro-Val-Gln-Val-Asp-Ala-Lys-Met-Pro-Pro-Leu-Phe-Leu (foam protein 4, SEQ ID NO: 4), Val-Tyr-Pro-Pro-Gln-Tyr-Pro-Gly-Met-Gly-Leu-Ile-Gln-Asn-Leu (foam protein 5, SEQ ID NO: 5) and Asp-Val-Val-Ala-Asn-Met-Leu-Pro-Leu-Phe-Leu-Ile (foam protein 6, SEQ ID NO: 6), respectively.

A search through the data bank "SWISS-PROT" revealed that all these sequences are novel proteins.

Example 2

Preparation of monoclonal anti-foam protein antibodies

Monoclonal antibodies directed to foam protein 1

Foam protein 1 obtained from Example 1 was used as an antigen to prepare monoclonal antibodies. At first, foam protein 1 was suspended in distilled water and adjusted to an appropriate protein level (1 mg/ml) with physiological saline (0.9 w/w % aqueous NaCl solution). This suspension was mixed with complete Freund's adjuvant in a volume ratio of 3:5 to prepare a water in oil emulsion. Three BALB/c mice (4 weeks old) were primed by intraperitoneal and subcutaneous injections of the emulsion in an amount equivalent to 0.18 mg/mouse of the antigen. A booster emulsion was similarly prepared with incomplete Freund's adjuvant and also intraperitoneally and subcutaneously injected into the animals in an amount equivalent to 0.09 mg/mouse of the antigen. The animals received three booster challenges at intervals of a week to 10 days.

Three days after the final challenge, the spleen was extracted and thoroughly washed with RPMI-1640 medium. The spleen cells ($1\times10^8$) were mixed with the parent cells ($2\times10^7$) (myeloma, P3X63Ag-U1), combined with 1.5 ml of a 50% solution of polyethylene glycol 1500 in RPMI-1640 and centrifuged at 1000 rpm for about 40 seconds. The solution was diluted by gradually adding 5 ml of RPMI-1640 medium and then centrifuged at 1000 rpm for 3 minutes. After the supernatant was discarded, 6 ml of HT (hypoxanthine-thymidine) medium was added and the mixed solution was again centrifuged at 900 rpm for 5 minutes. Then, the cells were dispersed in 20 ml of HT medium and a 100 µl aliquot was poured into each of 60 inner wells of 96-well culture plates, and on the following day, 40 µl of HAT (hypoxanthine-aminopterin-thymidine) medium was added. After then, a half of the medium was replaced by a fresh HAT medium every 3 days and the culture supernatant was tested for antibody titer after 14 days to show 12 positive wells. Then, limiting dilution was repeated several times by diluting these positive hybridomas with HT medium fed with BALB/c mouse thymocytes to finally obtain several hybridomas producing monoclonal anti-foam protein antibodies.

Thus obtained hybridomas were intraperitoneally injected into BALB/c mice which had been treated with pristane(2, 6, 10, 14-tetramethylpentadecane) and the ascites were collected after 2–3 weeks to obtain monoclonal anti-foam protein antibody raw fractions. These monoclonal antibodies were salted out by the sulfate ammonium method and purified by affinity chromatography on protein G.

The resulting monoclonal antibodies were screened for the reactivity with foam protein 1 obtained in Example 1. In this manner, several monoclonal antibodies including antibody A and antibody B were obtained.

Monoclonal antibodies directed to foam proteins 2–6

Two hybridomas directed to each of foam proteins 2–6 were obtained in the same manner as described above. The obtained hybridomas were intraperitoneally injected into BALB/c mice which had been treated with pristane and the ascites were collected after 2–3 weeks to obtain monoclonal anti-foam protein antibody raw fractions. These monoclonal antibodies were salted out by the sulfate ammonium method and purified by affinity chromatography on protein G.

Monoclonal antibodies C, D directed to foam protein 2, monoclonal antibodies E, F directed to foam protein 3, monoclonal antibodies G, H directed to foam protein 4, monoclonal antibodies I, J directed to foam protein 5 and monoclonal antibodies K, L directed to foam protein 6 were obtained.

Example 3

Quantitation of foam proteins in beer samples by sandwich assay

Foam proteins in beer were quantitated by the sandwich assay using monoclonal antibody A directed to foam protein 1 obtained in Example 2 and biotinylated monoclonal antibody B as follows:

1) At first, dilute antibody A as a primary antibody with an antibody-adsorbing buffer (0.01M PBS(−) containing 0.05–0.1% NaN$_3$, pH 7.5–8.5), dispense a 100 µl aliquot into each well of a 96-well plate and allow the antibody to adsorb at 4° C. overnight.

2) Then, remove the supernatant and wash the plate twice with a washing solution (0.01M PBS(−) containing NaN$_3$ and Tween-20, pH 7.5–8.5), then dispense 200 µl/1 well of a blocking solution (0.01M PBS(−) containing 1–3% BSA and NaN$_3$, pH 7.5–8.5) and incubate at 37° C. for one hour.

3) Prepare a dilution series of a beer sample with a diluent (0.01M PBS(−) containing 0.1% BSA and 0.05–0.1% NaN$_3$, pH 7.5–8.5). Separately prepare a standard dilution series of foam protein 1 and a diluted solution of biotinylated antibody B used as a secondary antibody with the purpose of drawing a calibration curve of the foam protein.

4) Wash the blocked 96-well plate twice with the washing solution, then dispense 100 µl/well of each of the diluted solutions of the beer sample and the foam protein and incubate at 37° C. for 1.5 hours.

Wash the plate twice with the washing solution, then dispense 100 µl/well of biotinylated antibody B as a secondary antibody and incubate at 37° C. for 1.5 hours.

5) Further wash the plate twice in the same manner, dispense 100 µl/well of streptavidin-conjugated alkaline phosphatase (1000-fold dilution, Dakopatts) and incubate at 37° C. for 30 minutes.

6) Subsequently, wash the plate further twice with the washing solution, dispense 100 µl/well of a substrate solution (disodium p-nitrophenylphosphate salt (PNPP) diluted in a diethanolamine solution (pH 9.0–9.5) containing MgCl$_2$) and incubate at 37° C. for 10–15 minutes, then quench with 50 µl of 1–3N NaOH and measure the absorbance at 405 nm by an automatic absorptiometer.

7) Plot the measured values of absorbance from the standard dilution series to draw a calibration curve for foam protein 1. This calibration curve can be used to calculate the concentration of foam protein 1 contained in each beer sample.

Example 4

Comparison of the sandwich assay with the prior foam protein assay by ELISA using polyclonal antibodies Foam proteins in various commercially available final beer products were determined by the sandwich assay of the present invention using monoclonal antibodies directed to foam protein 1 as described in Example 3, as compared with the prior assay (JPA No. 333223/95) using polyclonal antibodies against foam protein raw fractions (FIG. 1). The prior assay uses polyclonal antibodies against foam protein raw fractions as primary antibodies and biotinylated goat anti-rabbit immunoglobulin as a secondary antibody. The current head retention assay (SHV assay) as shown in Comparative example 1 was also run.

The results are shown in Table 2 which includes head retention in cm$^2$ as determined by the SHV assay and foam protein levels (mg/L) calculated from each calibration curve under the heads of the prior assay using polyclonal antibodies against raw foam protein fractions and the present assay.

TABLE 2

| Beer | SHV | Prior assay | Present assay |
|---|---|---|---|
| A | 137 | 42 | 5.25 |
| B | 147 | 51 | 6.50 |
| C | 78 | 34 | 3.67 |
| D | 122 | 39 | 4.99 |
| E | 94 | 32 | 4.64 |

A correlation factor derived from the above results showed a very good correlation between the sandwich assay of the present invention and the SHV assay (Comparative example 1) (correlation factor of 0.926: FIG. 1, B). This correlation factor was higher than the correlation factor between the prior assay and the SHV assay (0.896: FIG. 1, A). Similarly, a high correlation factor (0.965) was also obtained between the assay of the present invention and the prior assay.

This clearly shows that this sandwich assay can be applied to exactly presume head retention of beer.

Then, a standard dilution series of foam protein was prepared to compare the sensitivities of the sandwich assay and of the prior assay (Table 3). The sandwich assay had a sensitivity 60–100 times higher than that of the prior assay, showing that it can measure even a very minor amount of foam proteins.

TABLE 3

| Sensitivity comparison | | |
|---|---|---|
| | Prior assay | Sandwich assay |
| Detection limit (µg/L) | 323 | 81 |
| Quantitation limit (µg/L) | 969 | 243 |

Then, monoclonal antibodies C/D directed to foam protein 2 (hereinafter referred to as pair 1), monoclonal antibodies E/F directed to foam protein 3 (hereinafter referred to as pair 2), monoclonal antibodies G/H directed to foam protein 4 (hereinafter referred to as pair 3), monoclonal antibodies I/J directed to foam protein 5 (hereinafter referred to as pair 4) and monoclonal antibodies K/L directed to foam protein 6 (hereinafter referred to as pair 5) obtained in Example 2 were used to determine each foam protein in beer by the same sandwich assay as described above. In the respective pairs of monoclonal antibodies, C, E, G, I and K were used as primary antibodies while D, F, H, J and L were used as secondary antibodies.

The correlation between the results of measurements from the sandwich assay and the current head retention assay of beer (SHV assay; Comparative example 1) was evaluated. As a result, a very good correlation was observed therebetween (The correlation factors were 0.973, 0.967, 0.982, 0.917 and 0.971 in the order from pairs 1 to 5). The correlation factor between the prior assay (JPA No. 333223/95) and the SHV assay was 0.906. (All the tests were run on 8 samples.)

Example 5

Evaluation method of stabilizers

Stabilizers purchased from different suppliers (a total of 6 samples including 5 samples of silica gel and one sample of tannic acid) were added to mash at a concentration of 400 mg/L (however, tannic acid was added at a concentration of 50 mg/L) and reacted under stirring for 5 minutes with ice-cooling. However, the sample treated with tannic acid was allowed to stand at 0° C. overnight. Then, each mash was cooled and centrifuged (12000 rpm for 3 min) and then subjected to ELISA as described in Example 3 using a monoclonal antibody directed to foam protein 1. The results are shown in Table 4 (wherein stabilizer B is tannic acid while the others are silica gel). It proved that the residual level varies with the type of stabilizer.

TABLE 4

| Treatment with various stabilizers | |
|---|---|
| | Foam protein level (mg/L) |
| A | 7.2 |
| B | 6.9 |
| C | 7.4 |
| D | 7.2 |
| E | 6.2 |
| F | 7.1 |

Example 6

Evaluation method of raw materials of beer (barley malt)

Wort was prepared from different varieties of barley malts from different areas (a total of 4 samples including 1 sample of brown malt, 2 samples of pale malts and 1 sample of black malt) and foam protein contents in these samples were determined according to the procedure described in Example 3 above. Table 5 shows the results of the sandwich assay using monoclonal antibody A directed to foam protein 1 and biotinylated monoclonal antibody B. It proved that foam protein contents vary widely with malt type.

TABLE 5

| Various barley malts | |
|---|---|
| | Foam protein level (mg/L) |
| A (brown malt) | 7.9 |
| B | 43.8 |

TABLE 5-continued

| Various barley malts | |
|---|---|
| | Foam protein level (mg/L) |
| C | 22.1 |
| D (black malt) | 0.48 |

Similarly, wort was prepared from four different varieties of barley malts from different areas (varieties A, B, C, D) and foam protein contents in these samples were determined according to the procedure described in Example 3 above. FIG. 2 shows the results of the sandwich assay using monoclonal antibody pairs 1, 2, 3, 4, 5 directed to foam proteins 2 to 6. It proved that foam protein contents widely vary with the malt type.

Example 7

Evaluation method of raw materials of beer (barley)

Foam protein contents in samples of four different varieties of barley malts from different areas were determined according to the procedure described in Example 3 above. Table 6 shows the results of the sandwich assay using monoclonal antibody A directed to foam protein 1 and biotinylated monoclonal antibody B. It proved that foam protein contents vary widely with barley type.

TABLE 6

| Various barleys | |
|---|---|
| | Foam protein level (mg/L) |
| 1 | 84.8 |
| 2 | 51.5 |
| 3 | 75.2 |
| 4 | 45.1 |

Comparative example 1

Head retention assay (SHV - Schaumhaftvermoegen - assay)

This assay evaluates head retention of beer by testing foaming tendency and adhesion of foam on glass surfaces. Namely, the entire amount of beer is constantly poured at once into a graduated cylinder for 20 seconds and head retention is quantatively evaluated by measuring the amount of foam still retained on the wall of the graduated cylinder 30 minutes after completion of pouring by a planimeter. Head retention is expressed in $cm^2$ (see "Chemistry and Biology", Vol. 13, No. 8, p. 504–509 (1975).

What is claimed is:

1. A monoclonal antibody specifically recognizing a novel foam protein crucial for head retention of beer wherein said protein is characterized by:
   1) a molecular weight of about 48,000 daltons as determined by Western blot analysis,
   2) an amino acid sequence shown in SEQ ID NO:1,
   3) an amino acid composition wherein the ratio of the amino acids are: 5.8% Thr/Gln; 10.0% Ser/Asn; 13.3% Glu; 3.2% Pro; 9.4% Gly; 11.5% Ala; 0.6% Cys; 8.7% Val; 4.8% Ile; 11.6% Leu; 0.8% Tyr; 5.9% Phe; 4.1% His; 5.9% Lys; 1.4% Trp; 2.8% Arg.

2. A hybridoma producing the monoclonal antibody of claim 1.

3. A process for preparing the monoclonal antibody of claim 1, comprising the steps of growing the hybridoma producing said monoclonal antibody in vivo or in vitro and collecting the monoclonal antibodies from the culture or ascites.

\* \* \* \* \*